(12) United States Patent
Gunther et al.

(10) Patent No.: US 6,191,286 B1
(45) Date of Patent: Feb. 20, 2001

(54) IMIDOSILANE COMPOSITIONS

(75) Inventors: Michael L. Gunther, Danbury, CT (US); Eric R. Pohl, Mt. Kisco, NY (US); Herbert E. Petty, Bethel, CT (US)

(73) Assignee: OSI Specialties Inc., Greenwich, CT (US)

( * ) Notice: Under 35 U.S.C. 154(b), the term of this patent shall be extended for 0 days.

(21) Appl. No.: 09/140,473

(22) Filed: Aug. 26, 1998

(51) Int. Cl.$^7$ .......................... C07D 207/444; C07F 7/04
(52) U.S. Cl. ............................. 548/548; 556/419
(58) Field of Search ............... 548/548; 556/419

(56) References Cited

U.S. PATENT DOCUMENTS

| | | |
|---|---|---|
| 3,249,461 | 5/1966 | Grotenhuis et al. . |
| 3,755,354 | 8/1973 | Holub et al. . |
| 5,300,547 | 4/1994 | Hegenson et al. . |

FOREIGN PATENT DOCUMENTS

| | | |
|---|---|---|
| 508610 | 10/1992 | (EP) . |
| 29385 | 1/1989 | (JP) . |

OTHER PUBLICATIONS

Chemical Abstract No. 122:82378.
Chemical Abstract No. 111:98796.
Search of Chemical Abstract Database—Apr. 30, 1997.
Search of Chemical Abstract Database—Jul. 15, 1997.
Search of Chemical Abstract Database—Nov. 24, 1997.
Search of Chemical Abstract Database.
Raj. A. Sundar adn Lon J. Mathias, Glass Reinforced–Diallylbisphenol/Maleimide Composites with Modified Interphases.
K.L. Loewenstein, The Manufacturing Technology of Continuous Glass Fibres, 3rd revised ed. (Elsevier, Amsterdam, 1993)—pp. 237–291.
Comprehensive Handbook on Hydrosilylation (1992)—pp. 41–49 and 124–126.

*Primary Examiner*—Paul J. Killos
(74) *Attorney, Agent, or Firm*—Shirley S. Ma

(57) ABSTRACT

Unsaturated imidosilanes which are essentially free of siloxanes are taught herein for use surface treatments for inorganic solid materials. Novel methods to make such silanes, which do not yield water or siloxanes as a by-product are also taught. Compositions consisting essentially of imidosilane treated inorganic solid materials, resinous materials and optionally a free radical generator, especially glass fiber reinforced composites, are taught.

15 Claims, No Drawings

IMIDOSILANE COMPOSITIONS

BACKGROUND OF THE INVENTION

Organofunctional silane compounds have been employed in the treatment of a variety of surfaces, such as metal oxides, silicates, particulate siliceous fibers and pigments, and fibers such as glass fibers, steel fibers and aluminum fibers. (Metal surfaces are regarded as oxide surfaces because they are oxidized even though their subsurfaces are not.) Some organofunctional silane treatments involve coating such a surface with an organic, an aqueous-organic or aqueous solution of the silane either alone or in conjunction with other chemicals.

These treatments enhance bonding between the inorganic oxide and resinous media. Consequently, the silanes have utility as components in primers in the application of coatings, adhesives and sealants to inorganic oxide surfaces and as a filler pretreatment to improve the strength and structural integrity of filled resin composites such as those incorporating glass fibers. Such organofunctional hydrolyzable silanes are termed "Coupling Agents" or "Adhesion Promoters".

The efficacy of the organofunctional silane is dependent in large part on its ability to react chemically or bond with the resinous media. During the curing reactions of thermosetting resins, the reactivity of the organofunctional group needs to match the reactivity of the thermosetting resin or the curing agent. It must become part of the organic polymer that makes up the resinous media. In fabricating thermoplastic articles, the organofunctional silane also needs to become part of the resinous media, either by reacting with organofunctional groups on the polymers or grafting onto the polymer backbone.

The organofunctional silane need not react with all of the resinous media to achieve the enhancement in structural integrity of the article incorporating it. Often, the enhancements can be achieved if the silane reacts with only a part of the resinous media or with additives that are compatible with the resinous media. For example, virgin polypropylene destined for glass fiber reinforcement typically is compounded with maleated polypropylene (a.k.a. coupled polypropylene) as taught in U.S. Pat. No. 5,300,547. Maleated polypropylene refers to a graft or co-polymer of propylene and unsaturated organic acids or their anhydrides. For example, maleic anhydride commonly is reacted with propylene to make maleic anhydride-propylene co-polymers. The two polypropylenes, virgin and maleated, along with glass fibers are co-fed into a compounding extruder and pelleted. Glass fibers for this process are manufactured with surface treatments (sizing) to include silanes chemically compatible with the maleic anhydride. An amino silane, such as SILQUEST® A-1100™ 3-aminopropyltriethoxysilane, would be an example of a maleic anhydride compatible silane. The silane on the glass fibers and the maleated polypropylene form chemical bonds during compounding (extrusion). The silane does not react with the virgin polypropylene. This chemical bonding of the glass fiber to the maleated polypropylene is responsible for the performance advantages of the glass fiber reinforced polypropylene. One disadvantage of using maleated polypropylene is its cost relative to that of uncoupled or virgin polypropylene. Another disadvantage of using maleated polypropylene is that the maximum enhancements in structural integrity and strength are not achieved. The maleated polypropylene mixing or dispersion into the virgin polypropylene may not be uniform. Its ability to react chemically with the organofunctional group of the silane on the inorganic surface is inhibited by the presence of the virgin polyproplyene. The maleic functional groups of the polypropylene that do not react with the silane can contribute undesirable properties to the composite, such as making the resinous media more hydrophilic and, therefore, less resistant to degradation due to moisture. Achieving increased performance with glass fiber reinforced virgin polypropylene, by providing a glass fiber reactive toward the uncoupled (virgin) polypropylene, would be useful.

Moreover, other organic resins (e.g., nylon) used in conjunction with inorganic materials often have insufficient or non-reactive functional groups. New silanes that are effective at bonding with these materials are required (needed) to enhance the organic resin's properties when used with inorganic materials. Imidosilanes, when used alone or in combination with free radical generators are unique in their ability to couple with or bond to various resinous media.

Imidosilanes are known, see e.g., U.S. Pat. Nos. 3,755,354 and 3,249,461 and EP Patent No.0 50861, but these imidosilanes are problematic in that the presence of water is inherent in the method of manufacture of said silanes. Water causes hydrolysis of the silane to form siloxanes and turns the silanes from a liquid to a paste, which is unsuitable for uses in coating or sizing formulations that require the silane to be soluble and flowable over the surface of the inorganic surface. See, e.g., Example 1 of U.S. Pat. No. 3,755,354. Other synthetic methods result in the presence of chloride, which degrades the composite matrix.

SUMMARY OF THE INVENTION

The present invention teaches novel unsaturated imidosilanes and compositions incorporating these silanes. Moreover, novel methods of manufacture of these imidosilanes are disclosed which results in silanes essentially free of siloxanes and chloride.

DETAILED DESCRIPTION OF THE INVENTION

The present invention describes the improvement in wet and dry mechanical strengths of inorganic filler reinforced organic resin and in adhesion of organic resin to inorganic surfaces obtained by surface treating the inorganic surface or filler with an unsaturated imidosilane and optionally a free radical generator. The incorporation of fillers treated with ethylenically functionalized silanes, and optionally, free radical induced-grafting, offers even increased performance. Specifically, thermoplastic and thermoset resins that are reinforced with fillers, especially glass fibers, treated with an unsaturated imidosilane and optionally a free radical generator offer composites with dramatically enhanced wet and dry flex strengths.

Silane Structure

The unsaturated imido silanes of the present invention are of the formula (I) $((R^1)_bY)_aR^2_{3-a}SiR^3N(C=O)_2X$ wherein $R^1$ and $R^2$ are monovalent radicals, $R^3$ is a divalent radical, X is a divalent radical containing at least one ethylenic unsaturation, wherein both valences are attached to the carbonyl groups attached to the nitrogen (i.e., form a ring with the —C(=O)NC(=O)— group), Y is oxygen, nitrogen or sulfur, a=1 to 3, and b=1 or 2 depending on the valence of Y.

In formula I above, each $R^1$ is a monovalent radical, e.g., hydrogen, an imino group, a dialkyl amine, or, preferably a hydrocarbon functionality, including, but not limited to, aryl, allyl, cycloalkyl, alkyl (linear or branched) or aralkyl that may contain heteroatoms, e.g., oxygen, nitrogen or sulfur. $R^1$ could also be an acyl functionality (e.g., acetyl). Examples of $R^1$ are —N=C(CH$_3$)$_2$, and —CH=CHCH$_3$. Most preferably $R^1$ is an alkyl of 1 to 10 carbon atoms, e.g., methyl, ethyl, isopropyl, cyclohexyl, or i-butyl.

The value of b depends on the valency of Y. i.e., b=1 for Y=oxygen or sulfur, and b=2 for Y=nitrogen. Preferably Y is oxygen.

Preferably a is 3, but if a<3, each $R^2$ is a monovalent radical, including, but not limited to, a hydrocarbon radical, a saturated hydrocarbon, an unsaturated hydrocarbon or cyano. Preferably $R^2$ is a cycloalkyl, alkyl (linear or branched) or aralkyl, that may include heteroatoms, e.g., oxygen, nitrogen, or sulfur and 1 to 10 carbon atoms. Exemplary $R^2$ include, phenyl, phenylethyl or 2-methoxypropyl. Most preferably $R^2$ is methyl or ethyl.

$R^3$ is a divalent bridging group, including, but not limited to, an alkylene, alkenylene, alkarylene, arylene, or polyalkylene oxide, but preferably is a $C_1-C_{12}$ alkylene, e.g., propylene or n-butylene, and may be branched, e.g., neopentylene, cyclic, e.g., dimethylene cyclohexane, or unsaturated, e.g., dimethylene cycohexene or phenylene.

In novel silanes, $R^3$ may include a heteroatom substituents, e.g., $R^3$ may include an amino group either in the backbone or pendant to the backbone. Specific examples of $R^3$ are ethylene propylene amine, diphenylene amine, di(ethylene) ethyl amine. Such silanes, including specifically those with an amine in $R^3$, are advantageous because they allow for further chemistry to be performed during the composite fabrication process.

X is a divalent species wherein each valence is attached to a carbonyl group and each carbonyl group is attached to the nitrogen, thus forming at least one ring. Moreover, X contains, either internal or external to the ring, at least one ethylenic unsaturation. X may be a bicyclic species, with the unsaturation in either ring. Preferably X is a hydrocarbon that forms a ring of 5 to 12 atom with the imide group. Specific examples of X (which incorporate the imido (—C(=O)NC(=O)—) functionality) are (I) isobutenylsuccinimido, (II) (+/−)-2-octen-1-ylsuccinimido, (III) itaconimido, (IV) 2-dodecen-1-ylsuccinimido, (V) cis-1,2,3,6-tetrahydrophthalimido, (VI)

cis-5-norbornene-endo-2,3-dicarboxylimido, (VII)

endo-bicyclo[2.2.2]oct-5-ene-2,3-dicarboxylimido, (VIII)

methyl-5-norbornene-2,3-dicarboxylimido, (IX)

exo-3,6-epoxy-1,2,3,6-tetrahydrophthalimido, (X) maleimido, (XI)

citraconirimrnido, (XII) 2,3 dimethylmaleimido, (XIII)

1-cyclopentene-1,2-dicarboxylimido, (XIV) 3,4,5,6-tetrahydrophthalimido.

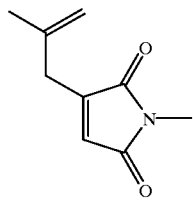

I

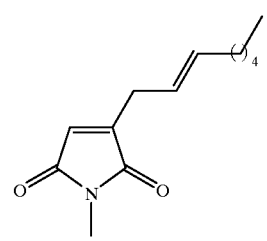

II

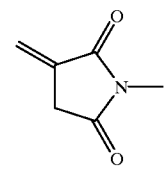

III

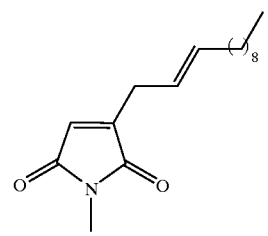

IV

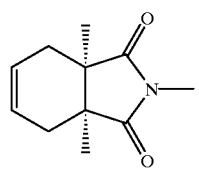

V

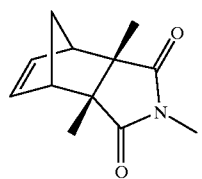

VI

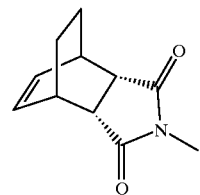

VII

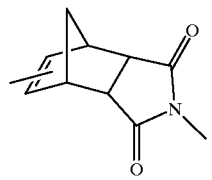

VIII

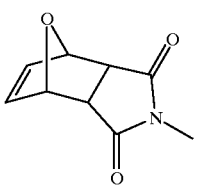

IX

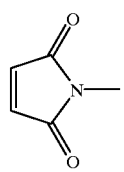

X

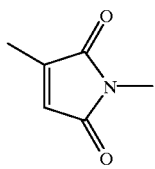

XI

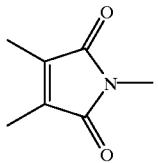

XII

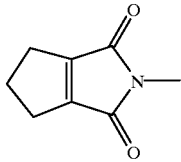

XIII

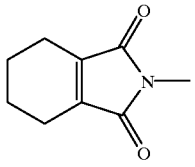

XIV

Preferably, the unsaturated imidosilanes are substantially free of siloxanes. Water generated during synthesis causes premature hydrolysis of the alkoxy silane to form siloxanes. Preferably, there is less than 5 percent siloxane by weight of silane, more preferably, less than 2 weight percent and most preferably less than 0.5 weight percent and even more preferably no siloxanes. Being essentially free of siloxanes is a result of the process of the novel methods of manufacture recited below. Such freedom from water provides benefits in not interfering with silane reactions. Moreover, the presence of water causes the alkoxy silane to hydrolyze and condense to a siloxane, said siloxane would be a solid or a paste and could not be used as such in the processing of glass fibers.

The silanes preferably should also be free of halogens, specifically, chlorine, since these halogens may be detrimental to the composite. Halogen levels should be below 1 weight percent, more preferably 0.01 weight percent, and most preferably at zero weight percent of halogen.

Compositions Containing the Silane

The silane may by encompassed within compositions that contain inorganic surfaces, such as fillers or flat surfaces, resinous media and optionally a free radical generator. The modes of incorporating the silane into these compositions included treatment of the inorganic surfaces with an organic, an aqueous-organic or an aqueous solution of the silane either alone or in conjunction with other chemicals, or coating the surface with the silane without the aid of a solvent. These silane treated surfaces then can be combined with the resinous media and optionally, a free radical generator. In some instances, the silane can be added directly to the resinous media in a process called "integral blending". The resinous media in conjunction with the inorganic surfaces treated with the silane can be employed, for example, for molding including extrusion, injection, calendering, casting, compression, lamination, and transfer molding, for coatings including lacquers, film bonding, paints, primers, inks, dyes, binders and glass fiber sizes.

The inorganic surfaces that can benefically treated with the silane are inorganic solid materials which possesses either oxide or hydroxyl groups at its exposed surface, and includes any material that can be treated by coupling agents known in the prior art. The inorganic solid material can be in any form, including particles or irregular or regular, e.g., spherical, shape, individual fibers, woven fiber mats or fabric, or continuous surfaces such as sheets, films, slabs and formed shapes.

Specific illustrations of suitably employed inorganic solids materials are, for example brass with surface oxidation, copper metal oxidized at its surface, iron, steel, alumina, aluminum trihydrate, siliceous materials such as fumed silica, hydrated silica, silica aerogels, aluminum silicates, calcium magnesium silicate, clays, mica, molecular sieves, wollastonite, E-glass, S-glass, A-glass and the like.

The amount of silane used is that amount which alters the surface characteristics of the inorganic solid material so that it is more compatible with and/or adherent to the resinous medium within which they are incorporated. When the silane is supplied to the resin by the integral blending method, the effective amount of the silane can vary from about 0.05 weight percent to about 15 weight percent and is preferably from 0.1 weight percent to 2.0 weight percent, based upon with weight of the solid inorganic material that is incorporated into the resin.

When the silane is supplied directly to the surface of the inorganic solid material in the form of a fibrous or particluate filler, pigment or the like, the effective amount can vary from about 0.01 weight percent to about 10 weight percent, and is preferably from 0.1 weight percent to about 0.5 weight percent based upon the weight of the inorganic solid material. When applying the silane as a primer to a surface of inorganic solid material, the effective amount of silane applied to the surface can vary from about 0.005 grams/$m^2$ to about 1.5 grams/$m^2$, and is preferably from about 0.01 grams/$m^2$ to 0.1 grams/$m^2$, calculated as the weight of the silane per square meter of inorganic solid material's surface treated.

The resinous medium can be a thermoplastic or thermosetting material, and the use of the term "resinous media" does not exclude the possibility that the material is formed in situ and therefore is derived from a monomeric material while in contact with an inorganic solid material. Preferably thermoplastic resins are used for the present invention.

The resinous medium with which the silane can be employed suitably includes a large number of resins which are reactive with the unsaturated imido functional group of the silane either alone or optionally with a free radical generator. For illustration purposes, the resinous media may be alkyd resins, unsaturated polyesters, vinyl esters, nylons, thermoplastic polyesters, polyethylenes, polypropylenes, polybutylenes, polystyrenes, styrene and butadiene copolymers, ethylene and propylene copolymers, SBR, natural rubbers., and the like. Most preferably polypropylene is used herein.

The size may include a free-radical generator, selected from the group of water soluble or oil soluble peroxides, such as hydrogen peroxide, ammonium persulfate, potassium persulfate, various organic peroxide, such as dialkyl peroxides, e.g., diisopropyl peroxide, dilauryl peroxide, di-t-butyl peroxide, di-(2-t-butylperoxyisopropyl)benzene; dicumyl peroxide, alkyl hydrogen peroxides such as t-butyl hydrogen peroxide, t-amyl hydrogen peroxide, cumyl hydrogen peroxide, diacyl peroxides, for instance acetyl peroxide, lauroyl peroxide, benzoyl peroxide, peroxy ester such as ethyl peroxybenzoate, and the azo compounds such as 2-azobis(isobutyronitrile). It is also invisioned that the free radical generator can be the resinous material, especially the thermoplastic resins, in conjunction with high shear processes. The high shear degrades the thermoplastic resins to generate radicals on the polymer backbone or at chain terminus.

The coatings that are used to treat the inorganic surfaces can be organic, aqueous-organic or aqueous solution of the silane either alone or in conjunction with other chemicals. The other chemicals are used as wetting agents, antistatic agents, leveling agents, binders, lubricants, fiber protectants, film formers and the like.

When the solutions of the silanes are used to treat glass fibers, they are called "sizings". Such compositions may include film-forming polymers usually in the form of emulsions, e.g, polyurethane, epoxy, unsaturated polyester, epoxyester, bisphenol-A epoxy, bisphenolic polyester, polyvinyl acetate, vinyl acetate and acrylic copolymers, polyethylene, ethylene vinyl acetate copolymers, melamine formaldehyde, and the like. The size may also include plasticisers, e.g., phthalates, phosphates, polyesters and the like. The size may also include a lubricant, e.g., cationic acid solubilized fatty acid amides, polyalkylene oxides, alkyl imidazoline derivatives, amide substituted polyethylene amines, microcrystalline waxes, aliphatic polyamines and the like. The size may include acids, (e.g., acetic acid or cis-butenedioc acid), water, surfactants, anti-foaming agents, emulsifying agents, or other silanes (e.g., ethylenically unsaturated silanes). Water is necessary within the size to activate the silane toward the glass fiber. The other chemicals used in the size are referenced in K. L. Loewenstein, *The Manufacturing Technology of Continuous Glass Fibres*, 3rd revised ed. (Elsevier, Amsterdam, 1993).

Adding the silane and water together within the context of the size allows for dispersion of the silane within the size; however, pre-combination of water and silane and allowing the size to age for >72 hours would result in a siloxane gel, which would not be useful.

Preferably the size is applied to glass fibers which are intended for incorporation into polymer composites. The manufacture of such compositions are known in the art. Resulting composites have enhanced wet and dry strength, enhanced wet out, and improved strand integrity.

Method of Manufacture

The imidosilanes are made from an amino alkyl dialkoxy silane or an amino trialkoxysilane (e.g., aminopropyltrialkoxysilane, or N-aminoethyl-3-aminopropylmethyldialkoxy silane) and an unsaturated acid anhydride. It is preferred not to use halogen containing silanes since they will result in the presence of undesirable halides. Such reaction results in a ring opened silane. Exemplary anhydrides to use are isobutenylsuccinic;

(+/-)-2-octen-1-ylsuccinic; itaconic; 2-dodecen-1-ylsuccinic;

cis-1,2,3,6-tetrahydrophthalic; cis-5-norbornene-endo-2,3-dicarboxylic;

endo-bicyclo[2.2.2]oct-5-ene-2,3-dicarboxylic;

methyl-5-norbornene-2,3-carboxylic; exo-3,6-epoxy-1,2,3,6-tetrahydrophthalic;

maleic; citraconic; 2,3-dimethylmaleic; 1-cyclopentene-1,2-dicarboxylic; and 3,4,5,6-tetrahydrophthalic.

This first step may be conducted in the presence or absence of a solvent, with or without heating, though it is preferred not to heat, which may cause the formation of water. Suitable solvents include, methylene chloride, chloroform, alcohols, aliphatic and aromatic hydrocarbons, and ethers.

The ring opened silane (i.e., amicacid silane) is treated with a capping material thereby avoiding the formation of water during cyclization. Preferably this step should be performed without heating. Suitable capping materials which are silylating agents include trialkylsilyl halides, bis-(trimethylsilyl)trifluoroacetamide, N,O-bis(trimethylsilyl)acetamide, N-methyl-N-trimethylsilyltrifluoroacetamide, 1-(trimethylsilyl)imidazole, N-trimethylsilyldiethylamine, hexamethyldisilazane, and mixtures thereof. Specifically, trimethylchlorosilane is useful.

Other capping materials are those which convert carboxylic acids to esters, such as chlorinated hydrocarbons, dialkyl carbonates, dialkyl pyrocarbonates, dialkyl sulfonates, diazomethane and the like. However, alcohols which are commonly used to convert acids into esters are not suitable because they generate water during the capping reaction. Preferably, this reaction step is done in the presence of an acid scavenger (e.g., a base) when the capping material generates hydrogen halides. The base is used to remove the halides. Suitable examples of the base, include triethyl amine, pyridine or dimethylamino pyridine or any tertiary amine.

The third step is the heating of the capped amic-acid silane to form an imidosilane. When the capping material is a silylating agent, two equivalents are required. The silylating agent reacts with both the hydroxyl group of the carboxylic acid and the N–H group of the amide. The temperature should be from 40 to 80° C. with a vacuum. During this step, the reaction product of the capping material (e.g., hexamethyldisiloxane (MM)) will be released incorporating the oxygen of the original anhydride. Said reacted capper preferably may be distilled or flashed stripped from the imidosilane. If the capping material forms a carboxylic acid ester, then the cyclization can be promoted by heating the amic-ester silane. The temperature should be from 40 to 220° C. and preferrably from 80 to 120° C. During this step, an alcohol will be formed.

The resulting product avoids the presence of siloxanes and results in low halide levels.

Another method to form the imidosilane, which avoids the formation of water (and siloxanes) is to react an unsaturated acid anhydride with an isocyanatosilane in one step, which process releases $CO_2$, as well as the imidosilane. A stoichiometric ratio of anhydride and isocyanate in the presence of a catalyst, preferably a phospholene, are heated at reflux, cooled and filtered.

Alternatively an unsaturated imide with a vinyl functionality may be hydrosilated with a hydrido alkoxy silane. The hydrosilation may conducted as known in the art. See, e.g., Marciniec, ed., *Comprehensive Handbook on Hydrosilylation* (1992), relevant portions of which are incorporated herein by reference.

A fourth, water free process is to start from a bis(amido silane), heat at about 190 to 240° C. (with or without catalysts), which will yield the imidosilane and an aminosilane.

EXAMPLES

Example 1
Synthesis of the Silane A

A 5000 ml reactor was placed under a nitrogen atmosphere (bubbler) and was charged with 352 g of ground maleic anhydride and 574 g of methylene chloride. With stirring, 796 g of SILQUEST® A-1100™ (Witco Corp.) 3-aminopropyltriethoxysilane was added to the reactor over a two hour period. The reactor was cooled to 10° C. using an ice-salt bath. 723 g of triethylamine was charged to the reactor. With continued cooling, 777 g of trimethylsilyl chloride was added to the reactor. Toward the end of the trimethylsilyl chloride addition, 300 g of methylene chloride was charged to the reactor and stirring was continued overnight. The reaction mixture was pressure filtered through a 30 µm then a 0.5 µm filter. The filtrate was placed into a 5000 ml flask and the methylene chloride was distilled from the flask at room temperature by slowly increasing the vacuum to 200 mm Hg. The cyclization to the final product was done under reduced pressure and gentle heating. The crude product was purified by vacuum distillation. $^1$H, $^{13}$C and $^{29}$Si NMR were consistent for maleimidopropyltriethoxysilane. This process is exemplified in Scheme I.

and analyzed by 29-Si NMR spectroscopy. The analysis indicated 35 mole percent siloxanes which indicates that water was present during the synthesis of the silane.

An attempt to prepare an aqueous solution of the silane in this present example was made. A mixture of 0.2 g silane, 0.1 g glacial acetic acid, 0.6 g methanol and 0.2 g water were stirred for 20 minutes. An additional 18.95 g water was added slowly with stirring. A yellowish solid precipitated almost immediately. A clear, stable and homogenuous aqueous solution of Silane A was prepared by the above mixing procedure.

Example 2
Treatment of Glass Fibers with Silane a Without Peroxide

A glass fiber sizing bath was prepared by adding a Silane A to a stock hydrolysis solution. The stock hydrolysis solution consisted of 1440 g of 2-propanol and 160 g of distilled water. This solution was adjusted to pH 4 with glacial acetic acid. A 0.5 percent (wt/wt) Silane A solution was prepared by adding 1.5 g of Silane A with stirring to 298.5 g of the stock solution. The solution was allowed to stir for an additional 30 minutes to insure complete silane hydrolysis. Fiber glass fabric was cut into strips and dipped into the silane solution. The strips were hung in a fume hood to air dry and placed in a 135° C. oven for 2.5 minutes.

Example 3
Treatment of Glass Fibers With Silane A and Peroxide

The treated glass fibers with Silane A from Example 2 were coated with a peroxide solution. A 0.15 weight (wt/wt) peroxide solution was prepared by dissolving 0.45 g of dicumyl peroxide in 299.55 g of toluene. The silane treated glass fabric strips were dipped into the peroxide solution and allowed to air dry for 1 hour.

Example 4
Preparation and Testing of Nylon Laminates Made From Silane A and No Peroxide

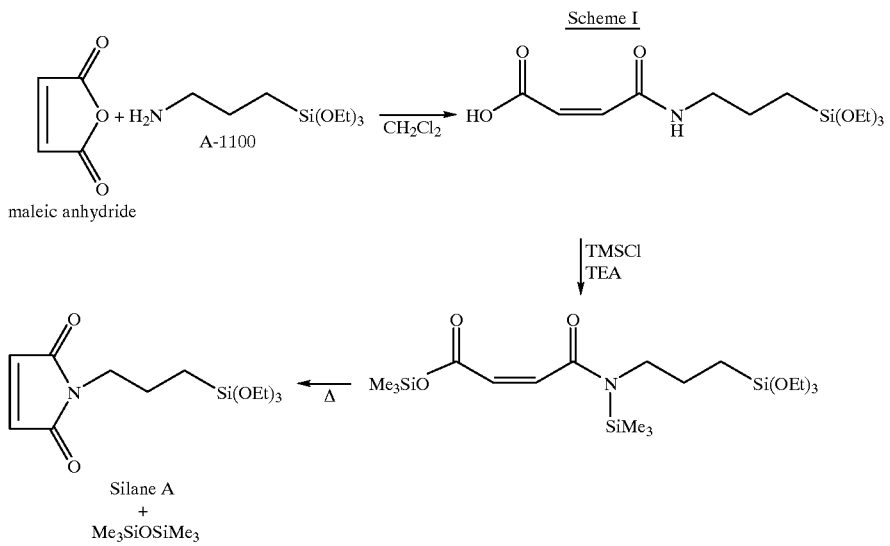

Comparative Example I
Synthesis of Maleimidosilane According to U.S. Pat. No. 3,755,354.

A mixture of 23.2 g 3-aminopropyltriethoxysilane, 10.3 g maleic anhydride, 0.53 g pyridine and 316 g hexane were charged into a 1000 ml, 3-neck round bottom flask equipped with a Dean Stark trap. The mixture was refluxed for 13 hours. Two layers formed. The lower layer was separated The treated glass fiber strips from Example 2 were were cut into 8 inch×8 inch (20.3 cm×20.3 cm) squares. Alternating layers of 10 mil (0.025 cm) nylon 6 film and treated glass fabric were used to make a 11-ply laminate. The laminates were pressed at 260° C. to a 0.125 inch (0.317 cm) stops with 1500 pounds (680 kg) ram force for 0.75 hour using a PHI press, model Q230H.

Specimens for dry and wet flex tests and loss-on-ignition (%LOI) analysis were cut using a diamond saw. The dimensions of the test specimens were 0.5 inch (1.77 cm) wide, 0.125 inch high (0.317 cm) and 3.5 inches (8.89 cm) long. The dry flex test were performed with a crosshead speed of 0.2 inches (0.51 cm) per minute and a 2 inch (5.08 cm) span width using an Instron 1123 tester according to ASTM D790. Wet flex tests were performed on specimens after 24 hour immersion in boiling water. The wet test were performed on the same size specimens and in the same manner as the dry samples. % LOIs were performed in accordance to ASTM D 4963-94. The results are presented in Table I.

Example 5
Preparation and Testing of Nylon 6 Laminate Made From Silane A and Peroxide The nylon 6 laminates were made and tested in a manner identical to Example 4 except that the treated glass fiber strips from Example 3 were used. The results are presented in Table I.

Comparative Example II

The treated glass fibers were prepared by the procedure in Example 2 except 3-aminopropyltriethoxysilane was used. The nylon 6 laminates were made and tested according to the procedures in Example 4. The results are presented in Table I.

Comparative Example III

The treated glass fibers were prepared by the procedures in Example 2 and 3 except the maleic acid amide silane was used. The silane was made by charging a 5000 ml reactor that was placed under a nitrogen atmosphere (bubbler) with 352 g of ground maleic anhydride and 574 g of methylene chloride. With stirring, 796 g of SILQUEST® A-1100™ (Witco Corp.) 3-aminopropyltriethoxysilane was added to the reactor over a two hour period. The methylene chloride was stripped from the flask at room temperature by slowly increasing the vacuum to 200 mm Hg.

The nylon 6 laminate was made and tested according to the procedures in Example 4.

Example 6
Preparation and Testing of Polypropylene Laminate Made From Silane A and Peroxide.

The treated glass fiber strips from Example 3 were were cut into 8 inch×8 inch (20.3 cm×20.3 cm) squares. Alternating layers of 15 mil (0.038 cm) polypropylene film and treated glass fabric were used to make a 9-ply laminate. The laminates were pressed at 232° C. to a 0.125 inch (0.317 cm) stops with 1500 pounds (680 kg) ram force for 1 hour using a PHI press, model Q230H. The laminates were tested according to the procedures in Example 4. The results are presented in Table I.

Comparative Example IV

The treated glass fibers were prepared by the procedures in Example 2 and 3 except vinyltrimethoxysilane sold by Witco Corp. under the tradename SILQUEST® A-171 was used. The laminate was prepared and tested according to the procedures in Example 6. The results are presented in Table I.

Comparative Example V

The treated glass fibers were prepared by the procedures in Example 2 and 3 except 3-methacryloxypropyltrimethoxysilane sold by Witco Corp. under the tradename SILQUEST® A-174 was used. The laminate was prepared and tested according to the procedures in Example 6. The results are presented in Table I.

Comparative Example VI

The treated glass fibers were prepared by the procedures in Example 2 and 3 except the silane prepared in Comparative Example III was used. The laminate was prepared and tested according to the procedures in Example 6. The results are presented in Table I.

Comparative Example VII

The treated glass fibers were prepared by the procedure in Example 2 except 3-aminopropytriethoxysilane sold by Witco Corp. under the tradename SILQUEST® A-1100 was used. The laminate was prepared and tested according to the procedures in Example 6. The results are presented in Table I.

Comparative Example VIII

The treated glass fibers and laminates were made according to Comparative Example VII except a maleated polypropylene film that it contained 1500 ppm grafted maleic anhydride. The results are present in Table I.

Comparative Example IX

The treated glass fibers and laminates were made according to Comparative Example VII except a maleated polypropylene film that it contained 3000 ppm grafted maleic anhydride. The results are present in Table I.

Example 7
Preparation and Testing of the Pultruded Polyester Rods Made From Silane A A glass fiber sizing bath was prepared by adding Silane A to a stock hydrolysis solution. The stock hydrolysis solution consisted of 1440 g of 2-propanol and 160 g of distilled water. This solution was adjusted to pH 4 with glacial acetic acid A 0.5 percent (wt/wt) Silane A solution was prepared by adding 1.5 g of Silane A with stirring to 298.5 g of the stock solution. The solution was allowed to stir for an additional 30 minutes to insure complete silane hydrolysis to the silanol form thereof. A water sized, single end roving containing 2040 filaments sold by Owens Corning under the name OCF 861 was dipped into the size bath at a draw rate of 25 foot per minute (762 cm per minute). The fibers were dried by passing them through a tube that was heated at 420° F. (215° C.) at a draw rate of 25 foot per minute (762 cm per minute) for a residence time of 0.8 minutes. The dried fibers wound up on a spool that was 36 inches (91.4 cm) in diameter for 22 revolutions. The fibers were removed from the spool, tie at one end and cut at the other end. The fibers were soaked in 1200 g AROPOL 7241 polyester resin sold by Ashland Chemical and 12 g of LUPERCO ATC, a solution of benzoyl peroxide in tricresylphosphate (50 weight percent) sold by Pennwalt, for 30 minutes. The soaked fibers were pulled into a 0.25 inch (0.635 cm) precision bored glass tube and cured for 30 minutes at 221° F. (105° C.). The rods were removed from the tube and cut into 2.25 inch (5.71 cm) lengths. The dry flex strength were determined according to ASTM D790 using an Instron 1123 tester with a crosshead speed of 0.2 inch (0.51 cm) per minute and a span of 1.75 inches (4.45 cm) The wet samples were boiled in water for 24 hours and tested in a similar manner. The loss-on-ignition (%LOI) was determined according to ASTM D 4963-94. The flex strength of the treated glass roving was determine by applying a force on a 1 inch (2.54 cm) span roving using an Instron 1123 tester at a crosshead speed of 0.2 in (0.51 cm) per minute. The value reported is the maximum force in grams necessary to bend the strand of glass. The results are reported in Table II.

Comparative Example X

The treated glass fibers and rod were made and tested according to Example 7, except that the silane was the maleic acid amide silane prepared in Comparative Example III. The results are present in Table II.

Comparative Example XI

The treated glass fibers and rod were made and tested according to Example 7, except that the silane was 3-methacryloxypropyltrimethoxysilane sold by Witco Corp. under the tradename SILQUEST® A-174. The results are present in Table II.

TABLE I

The test results for glass fiber reinforced laminates made with silane treated glass fiber cloth.

|  | Flex (dry) MPa | Flex (wet) MPa | Percent retention | Percent glass | Peroxide |
|---|---|---|---|---|---|
| Nylon Example |  |  |  |  |  |
| 4 | 468.5 | 254.9 | 54.4 | 58 | none |
| 5 | 427.2 | 206.7 | 48.4 | 53 | dicumyl |
| II | 372.1 | 179.1 | 48.1 | 54 | none |
| III | 420.3 | 227.4 | 54.1 | 54 | dicumyl |
| Polypropylene Example |  |  |  |  |  |
| 6 | 246.1 | 224.6 | 91.3 | 57 | dicumyl |
| IV | 170.9 | 150.2 | 87.9 | 52 | dicumyl |
| V | 144.7 | 125.4 | 86.7 | 51 | dicumyl |
| VI | 192.9 | 165.4 | 85.7 | 51 | dicumyl |
| VII | 124.0 | 96.5 | 77.8 | 47 | none |
| VIII | 199.8 | 179.1 | 89.6 | 52 | none |
| IX | 213.6 | 186.0 | 87.1 | 51 | none |

TABLE II

Test results of pultruded glass fiber rods made with silane treated glass rovings.

| Polyester Example | Flex (dry) MPa | Flex (wet) MPa | Percent retention | Percent glass | Glass Peroxide | Flex (g) |
|---|---|---|---|---|---|---|
| 7 | 764.8 | 716.6 | 93.7 | 61.5 | benzoyl | 61 |
| X | 737.2 | 496.1 | 67.3 | 62.3 | benzoyl | 37 |
| XI | 785.5 | 702.8 | 89.5 | 62.5 | benzoyl | 39 |

We claim:

1. An unsaturated imidosilane which silane is essentially free of mixture with siloxanes and halide, the silane having the formula:

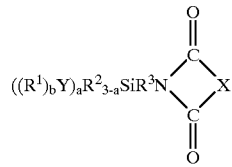

wherein $R^1$ and $R^2$ are monovalent radicals; $R^3$ is a divalent hydrocarbon radical, optionally substituted with a heteroatom substituent or interrupted with amine nitrogen or ether oxygen atoms; X is a divalent hydrocarbon radical containing at least one ethylenic unsaturation; a=1 to 3; and b is 1 if Y is oxygen or sulfur, or 2 if Y is nitrogen.

2. A silane according to claim 1 wherein X is a hydrocarbon group that forms a ring of 5 to 12 atoms with the imide group.

3. An unsaturated imidosilane which silane is essentially free of mixture with siloxanes and halide and has the formula:

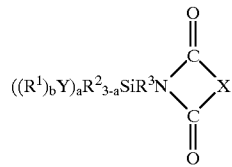

wherein $R^1$ and $R^2$ are monovalent radicals; $R^3$ is a divalent hydrocarbon radical, optionally substituted with a heteroatom substituent or interrupted with amine nitrogen or ether oxygen atoms; and wherein the structure $N(C=O)_2X$ is selected from the group consisting of (I) isobutenylsuccinimido, (II) (+/−)-2-octen-1-ylsuccinimido, (III) itaconimido, (IV) 2-docen1-ylsuccinimido, (V) cis-1,2,3,6-tetrahydrophthalimido, (VI) cis-5-norbornene-endo, (V) cis-1,3-dicarboxylimido, (VII) endo-bicyclo[2.2.]oct-5-ene2,3-dicarboxylimido, (VIII) methyl-5-norbornene-2,3-dicarboxylimido, (IX) exo-3,6-epoxy-1,2,3,6-tetrahydrophthalimido, (X) maleimido, (XI) citraconimimido, (XII) 2,3 dimethylmaleimido, (XIII) 1-cyclopentene-1,2-dicarboxylimido, and (XIV) 3,4,5,6tetrahydrophthalimido.

4. A silane according to claim 3 wherein a=3, Y=O and $R^1$ is either ethyl or methyl.

5. A silane according to claim 4 wherein a=2, Y=O, $R^2$ is an alkyl and $R^1$ is selected from the group consisting of hydrogen, an imino group, a dialkyl amine, a hydrocarbon functionality that may contain heteroatoms, and an acyl functionality.

6. A silane according to claim 1 wherein $R^3$ is selected from the group consisting of alkylene, alkenylene, alkarylene, arylene, and polyalkylene oxide.

7. A silane of the formula

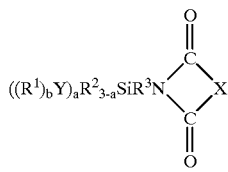

wherein $R^1$ and $R^2$ are monovalent radicals, $R^3$ is a divalent hydrocarbon radical which is substituted with a heteroatom substituent or interrupted with amine nitrogen or ether oxygen atoms, X is a divalent hydrocarbon radical containing at least one ethylenic unsaturation, Y is oxygen, nitrogen or sulfur, a=1 to 3, and b=1 or 2 depending on the valence of Y.

8. A silane according to claim 7 wherein $R^3$ includes an amino group either in the backbone or pendant to the backbone.

9. A silane according to claim 8 wherein $R^3$ is selected from the group consisting of diphenylene amine, and di(ethylene) ethyl amine.

10. A method of manufacturing an unsaturated imidosilane without producing water as a by-product, the method comprising (a) reacting an amino alkyl dialkoxy silane or an amino trialkoxysilane and an unsaturated acid anhydride to form an amicacid silane; (b) treating the amicacid silane with a silylating or esterifying agent capping material; and (c) heating the treated material to yield said imidosilane.

11. A method according to claim 10 wherein the acid anhydride is selected from the group consisting of: isobutenylsuccinic;

(+/−)-2-octen-1-ylsuccinic; itaconic; 2-dodecen-1-ylsuccinic;

cis-1,2,3,6-tetrahydrophthalic; cis-5-norbornene-endo-2,3-dicarboxylic;

endo-bicyclo[2.2.2]oct-5-ene-2,3-dicarboxylic;

methyl-5-norbornene-2,3-carboxylic; exo-3,6-epoxy-1,2,3,6-tetrahydrophthalic;

maleic; citraconic, 2,3 dimethylmaleic; 1-cyclopentene-1,2-dicarboxylic; and 3,4,5,6-tetrahydrophthalic anhydrides.

12. A method according to claim 11 wherein the capping material is selected from the group consisting of: trialkylsilyl halides, bis-(trimethylsilyl)trifluoroacetamide, N,O-bis(trimethylsilyl)acetamide, N-methyl-N-trimethylsilyltrifluoroacetamide, 1-(trimethylsilyl)imidazole, N-trimethylsilyldiethylamine, hexamethyldisilazane, chlorinated hydrocarbons, dialkyl carbonates, dialkyl pyrocarbonates, dialkyl sulfonates, and diazomethane.

13. A method of manufacturing an unsaturated imidosilane without producing water as a by-product, the method comprising reacting an unsaturated acid anhydride with an isocyanatosilane to yield $CO_2$ and said imidosilane.

14. A method of manufacturing an unsaturated imidosilane without producing water as a by-product, the method comprising hydrosilating an unsaturated imide with a hydrido alkoxy silane.

15. A method of manufacturing an unsaturated imidosilane without producing water as a by-product, the method comprising heating a bis(amido silane) to yield the imidosilane and an aminosilane.

* * * * *